United States Patent [19]
Smyth

[11] Patent Number: 6,092,058
[45] Date of Patent: Jul. 18, 2000

[54] AUTOMATIC AIDING OF HUMAN COGNITIVE FUNCTIONS WITH COMPUTERIZED DISPLAYS

[75] Inventor: Christopher C. Smyth, Fallston, Md.

[73] Assignee: The United States of America as represented by the Secretary of the Army, Washington, D.C.

[21] Appl. No.: 09/004,702

[22] Filed: Jan. 8, 1998

[51] Int. Cl.[7] .................................................. G06N 3/00
[52] U.S. Cl. ............................... 706/10; 706/16; 706/15; 600/554
[58] Field of Search ................... 706/10, 15, 16

[56] References Cited

U.S. PATENT DOCUMENTS

| 5,649,061 | 7/1997 | Smyth | 706/16 |
| 5,687,291 | 11/1997 | Smyth | 706/10 |
| 5,813,993 | 9/1998 | Kaplan et al. | 600/554 |

OTHER PUBLICATIONS

Sadasivan, P.K. et al.; "Neural Network Approach to the Enhancement of EEG Signals in the Presence of EOG Artefacts"; TENCON '91.1991 IEEE Region 10 International Conference on EC3–Energy, Computer, Communication and Control S.

Glover, J.R., Jr.; Raghaven, N.; Ktonas, P.Y.; Frost, J.D., Jr.; "Context–based automated detection of epileptogenic sharp transients in the EEG: elimination of false positives"; Biomedical Engineering, IEEE Transactions on; vol. 365, pp. 519–527, May 1989.

Chang, T.G.; Smith, J.R.; Principe, J.C., "A layered processing model for knowledge–based contextual interpretation of multichannel EEG/EOG signals", Southeastcon '88., IEEE Conference Proceedings, 1988, pp. 239–243.

*Primary Examiner*—Tariq R. Hafiz
*Assistant Examiner*—Edward G. Brown
*Attorney, Agent, or Firm*—Paul S. Clohan, Jr.

[57] ABSTRACT

An automatic aider of human cognitive functions for the operation of computerized displays. The invention estimates in real-time the mental decision made in response to a displayed stimulus from the single-even, transient, evoked cerebral potential and the corresponding visual response. The invention attains high accuracy levels of decision classification by combining a unique parametric model of the cerebral potential with advanced techniques drawn from numerical analysis, artificial intelligence, and nonlinear regression analysis. The invention uses an expert system to determine the decision aiding to be provided to the human operator from the disparities among the estimations and the decisions that are expected from task scripts for the displayed stimulus.

3 Claims, 9 Drawing Sheets

AUTOMATIC AIDING OF HUMAN COGNITIVE FUNCTIONS WITH COMPUTERIZED DISPLAYS

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

The present invention is based upon my earlier invention shown in U.S. Pat. No. 5,687,291 with the further improvements of: (1) a principal components analysis of event-averaged potentials to better model the human-cerebral sources, and (2) the inclusion of the attention state in the reliability estimate as determined from eye-movements. In addition, the present invention includes elements from my invention shown U.S. Pat. No. 5,649,061 relating eye fixations and brain wave analysis to decision making, and elements from my invention shown in U. S. Pat. No. 5,689,619 on the use of a fuzzy-logic processor to classify the attention state for display control from eye movement data.

The present invention estimates the decision made by a human as he performs cognitive functions in response to a displayed stimulus. The estimation follows from the corresponding single-event evoked, transient, cerebral potential, where the stimulus is typed by a definite task context. The evoked potential is generated naturally within the brain in response to the occurrence of the external stimulus. The amplitudes and latencies of the waveform components of the evoked potential are influenced by the properties of the stimulus and the mental processing that follows.

The present invention uses this decision estimate to provide real-time, automatic aiding for human interaction with an electronic information processing system when the operator is under a demanding cognitive work-load. The present invention may be used for the unintrusive measurement of cognitive functions as part of a training or testing regimen. Similarly, the present invention may be used to unintrusively monitor the state of a trained human operator for fatigue as part of an electronic safety net to detect degradation in operator performance on computerized tasks. In a more elaborate application, the present invention may be used as a component of an electronic "intelligent" human-computer interface for adaptive automated aiding of cognitive functions.

The present invention applies to computer controlled panel or head mounted video and aural displays used in manned crewstations such as helicopters, aircraft and other manned vehicles; display overlays on video returns in a control station for teleoperations of unmanned remote vehicles and platforms; and displays in communication, command and control stations such as modern air-traffic control or military tactical operations centers. Similarly, the present invention applies to head mounted displays used by an individual who, while netted electronically into a data distribution system, is performing stand-alone tasks such as assembly work, maintenance, or soldiering on the modern battlefield. These include computer controlled visual or aural overlays in head mounted video displays used for virtual reality, stereographics, monocular or binocular vision, and image enhancements for night vision.

There is little prior art for accurately estimating a cognitive decision from the corresponding single-event evoked, transient, cerebral potential. There has been prior work done in the laboratory on the mental control of machines by event averaged evoked cerebral potentials. For example, the amplitude of the P300 component of the event averaged transient potential has been used to select video display cues from a set of randomly repeated cue markers. The transient potential duration is on the order of several 100 milliseconds; however, and event averaging by using repetitive signals demands an unnaturally long attention on the order of 10 seconds by the human operator to the cue markers. The result is a procedure that would interfere with the real-time performance of most tasks.

In another example, the power spectrum of a visually evoked steady state potential has been used to select a visual display cue from a field of display cues with different flash rates. The power spectrum will have a peak at the flash rate for the gazed display cue. However, the power spectrum of the steady state potential is computed from the Fourier transform of a windowed signal of several seconds duration. This process is a form of short term averaging which requires forced visual fixation by the operator on the cue marker and for this reason tends to interfere with task performance.

In still another example reported by G. McMillan in a 1995 publication entitled "Brain-Actuated Control: Thinking ahead to Firefox" (Cseriac Gateway), the changes induced by a subject in the power spectrum of a visually evoked steady state potential, generated while looking toward a 13.25 Hertz flashing light, have been used to control the turn direction of a flight simulator, either left or right. Again, the power spectrum of the steady state potential is computed from the Fourier transform of a windowed signal of several seconds duration, and this short term averaging requires forced concentration by the operator which interferes with task performance. Furthermore, the light source must be intense, flashing (near critical fusion frequency) and within the vision-field of the human subject.

One method for estimating a cognitive decision from the corresponding single-event evoked, transient, cerebral potential follows from the work of S. Cerutti, G. Chiarenza, D. Liberati, P. Mascellani, and G. Pavesi in a 1988 publication entitled "A parametric method of identification of single-trial even-related potentials in the brain" (IEEE Transactions of Biomedical Engineering). These researchers used a parametric method for identifying single-trial, transient, event-related potentials in the brain. Their method assumes a moving average, autoregressive (ARMA) filtering model of the cerebral potential with the stimulating event as an exogenous input. The solution for the cerebral potential is recursively computed from the filtering model where an event average response potential is used as the initial estimate.

U.S. Pat. No. 5,649,061 was awarded to me on an apparatus and method for estimating from the cerebral potential, a decision made for selecting a display icon. The concept of a cerebral source is used with the moving average, autoregressive filter model of Cerutti et al. to parameterize the cerebral potentials. The technique uses an artificial neural network as a decision classifier with inputs consisting of the ARMA coefficients from the Cerutti et al. filter model applied to the transient cerebral potential collected during the visual fixation on the icon, as well as parameters from the visual response. These parameters include the duration of the fixation, the pupil dilation, and the number of eye blinks following the fixation. Essential to the success of the technique is the alignment of the recorded cerebral potential with the start of the fixation and windowing of the data to match the duration of the visual fixation. Lower order decisions of visual recognition and selection are processed during eye fixations.

In a supporting development, my invention shown in U.S. Pat. No. 5,726,916 (TEC JA251) shows an eyetracker that uses electrooculograms to provide the millisecond time resolution of eye movements that is needed to accurately align the fixation with the cerebral potential. This apparatus integrated with the apparatus of U.S. Pat. No. 5,583,795 for an optical eyetracker with head mounted displays, will maintain spatial alignment independent of any shifts of the facemask that is used to hold the electrodes and corrects for long term drifts in skin-surface potential.

The reasoning of Cerutti et al. for the recursive solution process of the moving average, autoregressive model of the cerebral potential is intuitive in nature. They do not provide a stated mathematical basis for their reasoning and computational stability is not necessarily assured by their approach. My invention shown in U.S. Pat. No. 5,687,291 replaces the moving average filter component with a parallel attenuator circuit design to better model the internally located cerebral source. The attenuator values are used as inputs to an artificial neural network decision classifier. The method described in the application has proven to be more effective then that developed by Cerutti et al., at least in computer simulation studies.

In another related development, my U.S. Pat. No. 5,689,619 shows an automated adaptive aider for the control of heads-up displays by eyetracker from display menus. This invention employs a fuzzy logic processor to classify the visual attention state from eye movement data and select a cuing format for the estimated state. This invention automatically provides time and spatial locating cues to aid the human operator as the conflict for attention among multiple tasks becomes more intense.

In the present patent application, the techniques of the above referenced patents are further embodied in a novel design for an automated aider of cognitive functions. The parallel attenuator circuit model of my invention shown in U.S. Pat. No. 5,687,291 is further embodied with the novel use of a set of independent basic waveforms to better represent the internally located cerebral sources generated in response to external stimuli. In this development, the basic waveforms are derived from a principal components analysis of the differences among event-averaged potentials. Also, the decision classifier of my invention shown in U.S. Pat. No. 5,649,061 is further embodied with inputs for the cognitive and visual attention states of the human. In support of this application, the method of U.S. Pat. No. 5,689,619 in which a fuzzy logic processor is used to classify visual attention for aiding display control is expanded to the processing of visual information in general. Finally, the alignment of the cerebral potential record with the visual fixation used in U.S. Pat. No. 5,649,061 is relaxed to enable the processing of higher order decisions beyond those needed for display control.

BRIEF SUMMARY OF THE INVENTION

It is therefore an object of the present invention to estimates the decision made by a human as he performs cognitive functions in response to a displayed stimulus.

Still other objects and advantages of the present invention will become readily apparent to those skilled in this art from the detailed description, wherein only the preferred embodiment of the present invention is shown and described, simply by way of illustration of the best mode contemplated of carrying out the present invention. As will be realized, the present invention is capable of other and different embodiments, and its several details are capable of modifications in various obvious respects, all without departing from the present invention. Accordingly, the drawings and descriptions are to be regarded as illustrative in nature, and not as restrictive.

These and other objects are achieved by the present invention which accurately estimates in real-time the mental decision made to a displayed stimulus from the single event evoked, transient, cerebral potential and the corresponding visual response. The present invention attains these high accuracy levels by combining a unique parametric model of the cerebral potential with advanced techniques from numerical analysis, artificial intelligence, and nonlinear regression analysis to classify the decision.

The present invention parameterizes the cerebral potential from an estimate of the responses of the underlying cerebral sources to the displayed stimulus. The present invention does this with a linear expansion of a set of orthonormal basic waveforms which are used to model the cerebral sources. These basic waveforms are computed by a principal components analysis of the event averaged potential differences derived in a neuro-psychological calibration process for the display stimuli set. A varimax rotation maps the basic waveforms to physiological sources within the cerebrum. The cerebrum is modeled electrically as an autoregressive filter with an input which is the summed output of a parallel set of attenuators. In turn, the inputs to the attenuators are the set of source basic waveforms and the attenuations of the circuit model are the linear expansion coefficient weights. The present invention computes the attenuation values of the parallel attenuator circuit from the measured cerebral potential and the basic waveforms of the internal sources. The set of attenuations is used in the invention to parameterize the response potential.

The present invention estimates the ability of the human operator to make a cognitive decision from the cerebral electroencephalogram. The present invention determines the reliability of the computed parameters from the estimated cognitive state with an expert system having production rules on cognitive functions. The expert system determines the cognitive state from the power spectrum of the autoregressive coefficients for the filter representation of the cerebrum.

In a further embodiment, the present invention uses an array of recording sites placed over the scalp for a more accurate determination of the cerebral response and cognitive state. The present invention computes source response parameters for each of the recording sites and uses the corresponding autoregressive coefficients from the recording electroencephalograms as input to the expert system for state determination.

The present invention estimates the ability of the human operator to notice and respond to the displayed stimulus. The present invention determines the human visual response and his state of attention with a fuzzy-logic processor, from the eye gaze statistics collected during the stimulus display.

The present invention uses these estimates to classify the mental decision made by the human operator in response to the displayed stimulus. The present invention classifies the decision with an artificial neural network which has inputs comprised of the set of attenuation values used to represent the cerebral sources, the cognitive reliability, visual response indexes, and the attention state. The outputs of the network are the probabilities of the occurrences of the set of possible task-related decisions that can be made in response to the display stimuli set.

The present invention determines the decision aiding to be provided to the human operator with an expert system which is driven by the disparities among the output probabilities from the classifier, and the decisions that are expected from task scripts for the displayed stimulus.

DETAILED DESCRIPTION OF THE INVENTION

Figure 1:
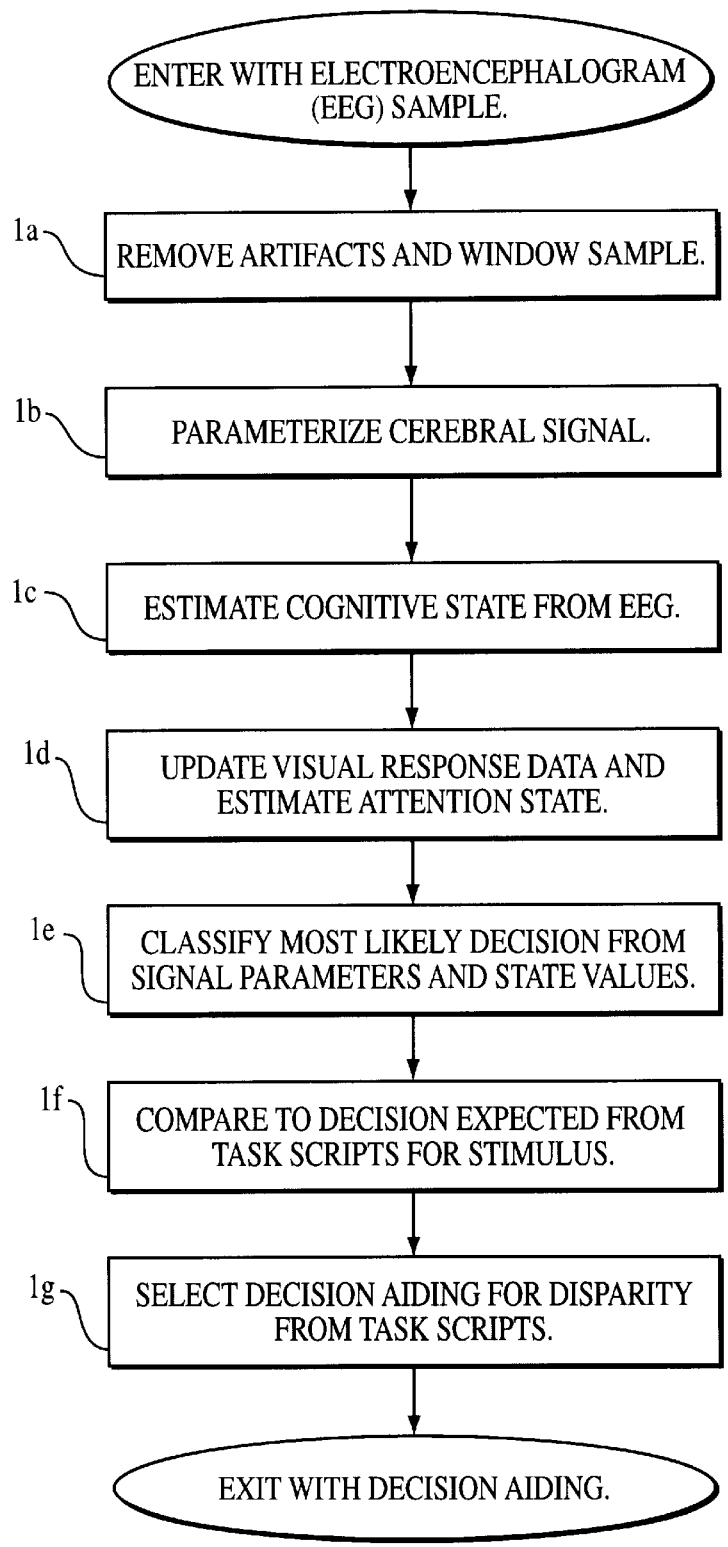
FIG. 1 is a flowchart of the method for automatically aiding a cognitive decision from the cerebral potential response of the human to a displayed stimulus.

The present invention continually estimates the decision made in response to the displayed stimuli according to the process flowcharted in FIG. 1. First, the recorded cerebral potential is corrected for artifacts (step 1a) and windowed to form a data sample. Next, the resulting signal is parameterized (step 1b) by computing the coefficients of an autoregressive filter representation for the recorded cerebral potential and the attenuations of a parallel attenuator model for the cerebral sources. The cognitive state is determined (step 1c) from the power spectrum of the autoregressive coefficients and the reliability of the estimated decision is computed from an expert knowledge of cognitive processes. The response to the stimulus is updated (step 1d) and the attention state is estimated from the response history. The set of attenuations, cognitive reliability, attention state, and stimulus response are the inputs (step 1e) to a decision classifier. The outputs of the classifier are the probabilities of the set of possible decisions which can be made in response to the displayed stimulus. In one embodiment, the strongest output of the classifier exceeding a threshold is selected as the best estimate of the decision made. The present invention then uses an expert system with production rules (step 1f), based on the disparities among the decision estimations and the decisions that are expected from task scripts for the displayed stimulus, to determine (step 1g) the decision aiding to be provided to the human operator.

Figure 2:
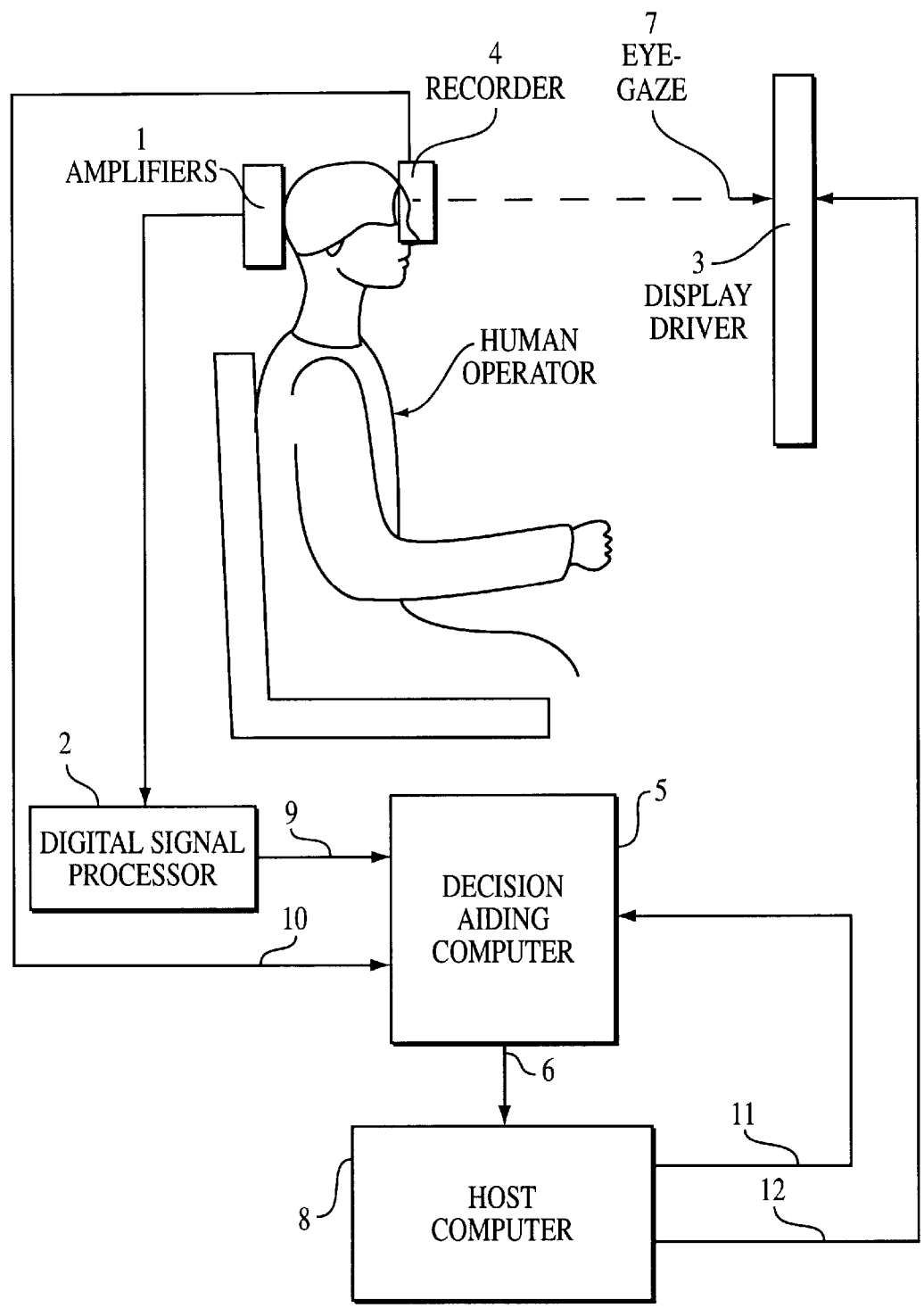
FIG. 2 is a schematic showing the hardware of the present invention.

The present invention, as shown in the schematic of FIG. 2, consists of the following components:

(a) an array of analog amplifiers 1 for recording human biosignals with analog electrical outputs,
(b) a digital signal processor 2 for determining the electroencephalogram with analog electrical inputs connected to the outputs of the amplifiers 1, and digital electrical output 9,
(c) a stimulus driver 3 with digital electrical input 12 from a host computer 8 and signal output in human sensory formats,
(d) a recorder 4 of operant responses for recording the head and eye movements of the human, with digital electrical output 10; and
(e) a digital computer 5 with digital electrical inputs connected to the outputs of the host computer 8, the operant recorder 4, and the digital signal processor 2, with the digital output 6 of the cognitive decision aiding.

The biosignal amplifier array 1 contains instrumentation amplifiers with inputs connected to skin-surface electrodes. An array of scalp-surface electrodes measures the electroencephalogram (EEG); another array of skin surface electrodes (not shown in the figure) measures the electrooculogram, electromyograms and electrocardiogram for artifact corrections. In one embodiment, the scalp-surface electrodes used to measure the EEG are in a multiple array configuration embedded in a helmet design with an indifferent electrode and amplifier ground. The electrode array is centered about the central and parietal cerebral scalp sites to reduce artifacts from extra cerebral sources while maximizing reception of the evoked cerebral potentials. The electrodes are recessed in the helmet and employ a gel impregnated floating sponge as bridge to the scalp skin surface.

Several electrodes are used to measure pertinent electromyograms (EMG) generated by the facial, shoulder, and arm muscles. These muscle-signals are measured using skin surface electrodes in a bipolar configuration which are adhered to the skin over the appropriate muscle sites. The Electrocardiogram (EKG) is measured with an augmented unipolar electrode, Einthoven's triangle chest cluster with amplifier ground, a configuration commonly used with exercising subjects. Finally, the electrooculogram (EOG) is measured with a periocular electrode array about the eyes, with two electrodes located horizontally at opposing temporal canthi sites, and two more electrodes located vertically at opposing sites one above the eyebrow and the other below the eye.

The digital signal processor 2 continually estimates the electroencephalograms (EEG) for the scalp electrode sites of the cerebral recordings from the electrical outputs of the bio signal amplifier array 1, following corrections for cerebral artifacts with the electrooculogram, electromyograms and electrocardiogram. The analog voltage outputs from the instrumentation amplifiers 1 for the skin surface electrode measurements are electrical inputs to a multiplexed analog to-digital converter acting as the front-end of the digital processor 2. The digital processor performs several filtering operations on these signals to extract the corrected electroencephalogram. First, the digitized cerebral signals are inputs to a programmable estimator filter in series with a predictor filter with an output which is the positive input to a digital summer. Next, the digital outputs for the extra cerebral signals from the modular 1 are input to an array of programmable estimator filters and predictor filters in series with outputs which are the corrective inputs to the digital signal summer. This design results in the cerebral artifacts being removed from the EEG signal following the inverse filtering of the site measurements. Finally, the output of the summer is the corrected electroencephalogram. The output from the processor 2 is the multiplexed electroencephalograms for the separate cerebral recording sites, and this output is the digital electrical input 9 to computer 5.

The stimulus driver 3 controls the presentation of the stimulus to be processed by the human operator. As examples, the stimulus driver may be a visual display driver or an aural controller for a sound speaker system. The driver is activated by a control line 12 from the host computer with the control line dictating the stimulus to be presented for the task being performed.

The operant recorder 4 records the observable response of the human operator to the stimulus from the stimulus driver 3. In particular, the recorder 4 records the orientation and attention of the human operator to the stimulus for the purpose of information processing. Note that the stimulus driver 3 and the operant behavior recorder 4 need to operate in compatible human sensory modalities. As an example, the figure shows a visual display as the stimulus driver 3 and an eyetracker as the operant behavior recorder 4; the eyetracker determines when the eye-gaze 7 of the human operator is directed onto the particular visual display cue which is the displayed stimulus.

The output of the digital computer 5 is a specification of the cognitive aiding to be provided to the human operator to help him in his task of processing the presented stimuli. The digital computer computes an estimate from the recorded cerebral potential of the cognitive decision made while the human processes the stimulus. In application, the aiding output may in turn be used in a feedback loop to control the stimulus to the operator. For example, FIG. 2 shows that the digital output 6 from the computer 5 is an input to a host computer 8 which is controlling the stimulus driver 3.

Figure 3:
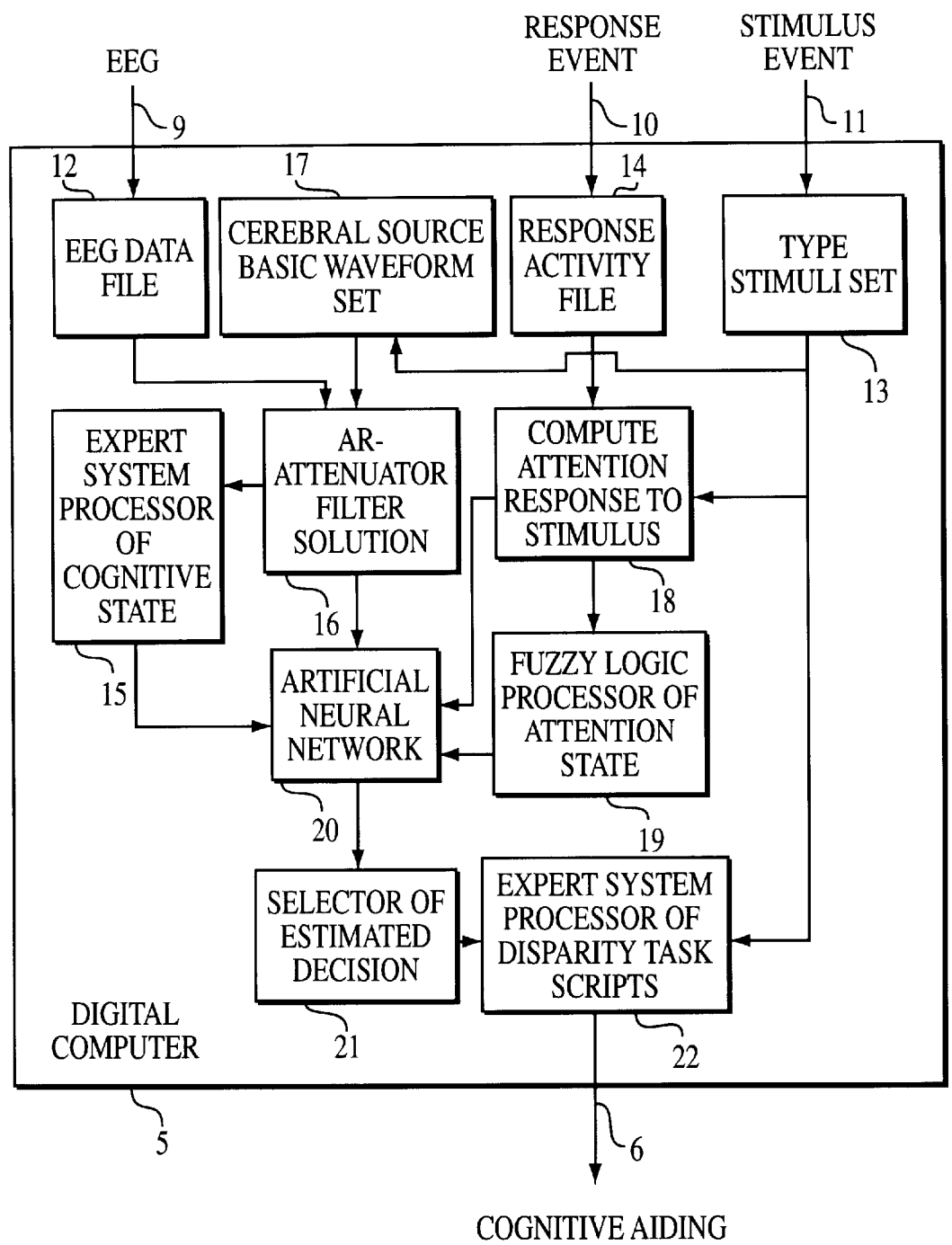
FIG. 3 is a flowchart of the computer functions.

The software routines of the digital computer 5 are flowcharted in FIG. 3. In a further embodiment, the computer routines are performed by digital processors embedded in a host computer. The routines are as follows:

a) a routine 12 which reads the electroencephalogram (EEG) output of the digital processor 2 from input 9, updates a time-serial data file, and forms a windowed cerebral potential sample from the data file for each cerebral recording site;

b) a routine 13 which upon receipt of a control line pulse 11 from the host computer 8 types the stimulus for the task being performed;

c) a routine 17 which flags the basic waveform set for the cerebral sources which are evocable by the stimuli-type;

d) a routine 16 that parameterizes the cerebral potentials by solving for the attenuator values and autoregressive coefficients of an autoregressive filter model of the cerebral potential driven by a parallel attenuator circuit with basic waveform sources;

e) an expert system routine 15 that estimates the mental state from the power spectrums of the autoregressive coefficients with an embedded knowledge on human cognitive processing and converts the state estimate to a reliability measure;

f) a routine 14 which reads the input 10 from the operant recorder 4 and updates a time-serial file of the response activities and in particular the visual fixations and eye movements;

g) a routine 18 which computes the orienting and attention response of the human to the stimulus, and in particular, the visual gaze points, durations, and transitions;

h) a fuzzy logic routine 19 that computes the attention state from the response activity, and in particular, the visual attention state from the gaze statistics;

i) a classifying routine 20 for an artificial neural network that estimates the decision made from the set of attenuator values, the cognitive reliability, the attention state, and the attention response to the stimulus;

j) a routine 21 for selecting the estimated decision from the outputs of the classifier; and k) a routine 22 that determines the decision aiding 6 from an expert system with production rules based on the disparities among the decision estimations and the decisions that are expected from task scripts for the displayed stimulus.

Figure 4:
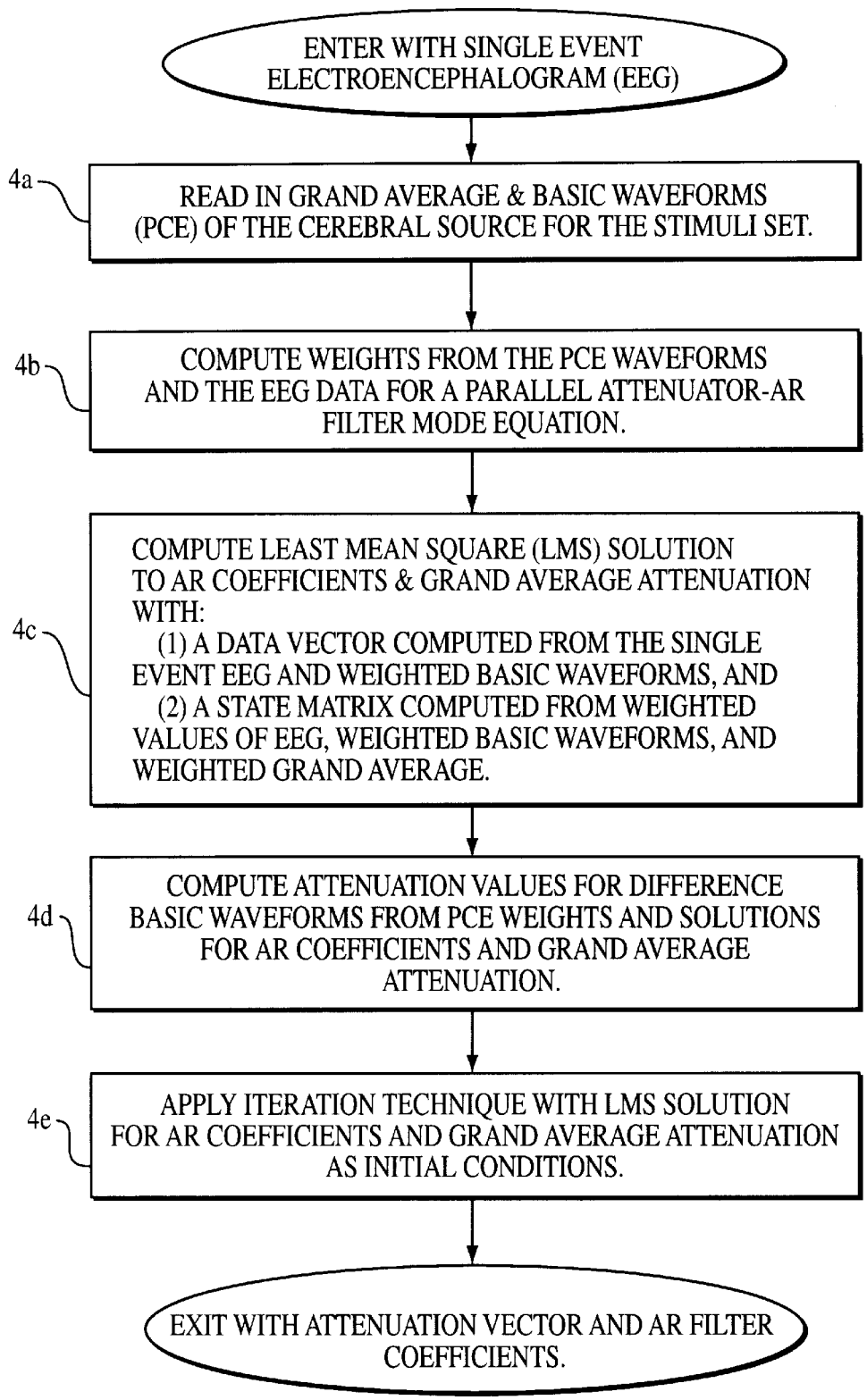
FIG. 4 is a flowchart of the routine used to compute the attenuations and the coefficients of the cerebral source, autoregressive filter model.

FIG. 4 outlines the method used in software routine 16 to compute, for each recording site, the cerebral potential filter model coefficients and the corresponding source attenuating values from the single event cerebral potential, given the grand average and basic waveforms for the stimuli set (4a). Weight values are computed (4b) for a parallel attenuator and autoregressive filter model from the cerebral potential and the basic waveforms. The autoregressive coefficients and grand average attenuation are next computed (4c) by the least means square procedure. In this process, the data vector is computed from the cerebral potential and weighted basic waveforms, and the state matrix is computed from the weighted values of the potential, basic waveforms, and the grand average. The attenuation values for the basic waveforms are then computed (4d) from the weights and the autoregressive coefficients and grand average attenuation. Finally, the computations of the basic waveform attenuations are refined (4e) with an iterative procedure.

Figure 5:
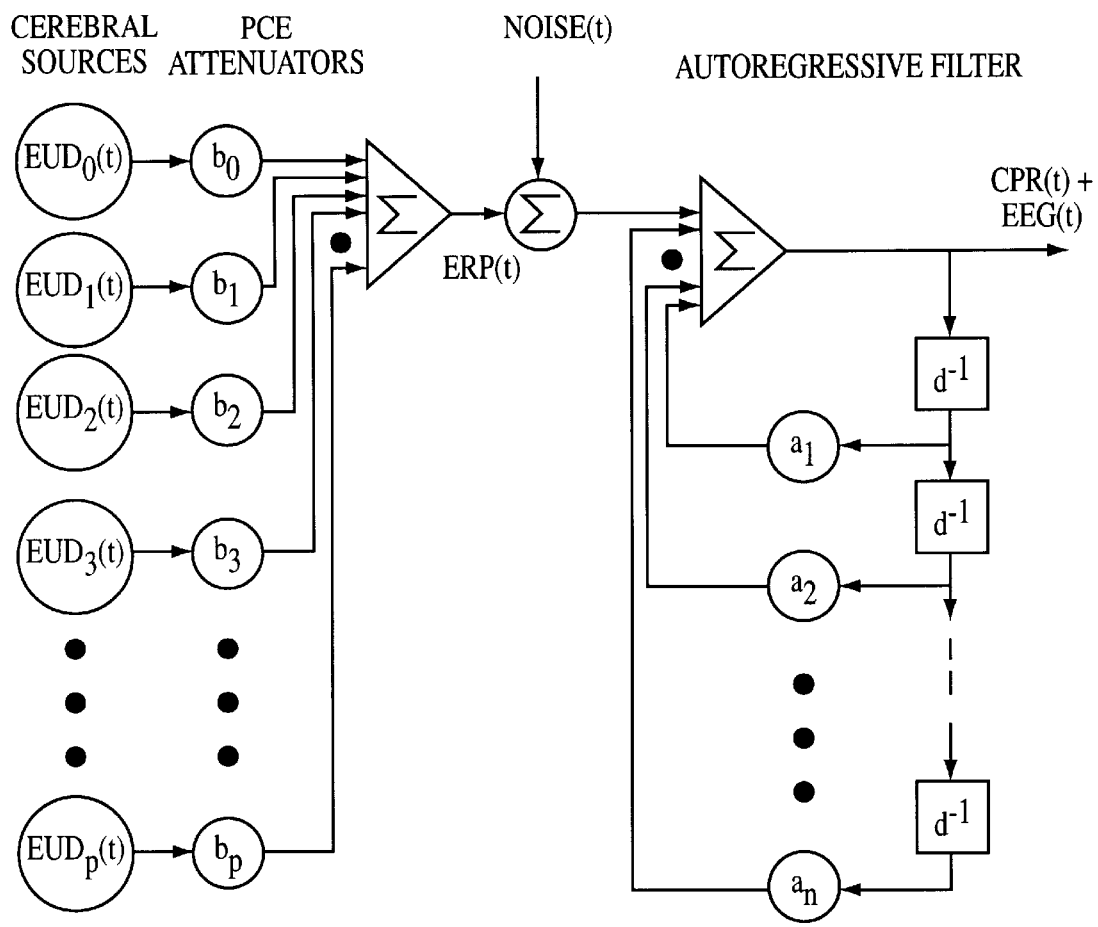
FIG. 5 is a schematic of the cerebral source attenuators and autoregressive filter model for the cerebral potential.

The solution method of FIG. 4 is derived from a realistic model of the cerebral potential. As shown in FIG. 5, the recorded cerebral potential (CPR) consists of a single event, evoked response potential (ERP) added to the background electroencephalogram (EEG). The potential is mathematically the output of an autoregressive filter which is used to model the electrical transmission of the cerebrum. The cerebral response to the stimulus is the deterministic input to the filter. The response is generated by a cerebral source (CDS) which in actuality is made up of a set of sources distributed internally throughout the cerebrum. These sources are modeled as the inputs to a parallel set of attenuators the sum of the outputs of which is the deterministic input to the autoregressive filter. The attenuations of the attenuator circuit change values with cognitive changes to produce the variation in the single event response.

The background electroencephalogram (EEG) is the sum of signals generated by multiple various and sundry sources within the brain which are continually occurring in a random manner uncorrelated to the stimulus. For this reason, the multiple sources of the background EEG make up a stochastic process which act as a random noise source. The output of this noise source is summed with the output of the attenuator circuit to form the input to the autoregressive filter. The coefficients of the autoregressive process reflects the mental state for cognitive processing, and therefore the ability to actively respond to stimuli and make decisions.

The development of the solution method from this filter model is now described in detail. Referring back to FIG. 5, the recorded cerebral potential (CPR) is the sum of the evoked response potential (ERP) and the background electroencephalogram (EEG). In equation form, the Kth sample of the recorded cerebral potential, here denoted by cpr[K], is given by the weighting of the prior n samples, the internally located cerebral source potential, cds[K], the stochastic noise source, e[K], as follows:

$$cpr[K]=cds[K]+a_1*cpr[K-1]+a_2*cpr[K-2]+\ldots+a_n*cpr[K-n]+e[K], \quad (1)$$

where the filter is an nth order autoregressive process with coefficients ($a_1, a_2, \ldots a_n$). The equation applies to all the Nth samples in the recording from the start to the end of the evoked response (K=0,1, ..., N−1), where for samples before the stimulus event (K<0), the cerebral source potential is zero and the potential recordings are the background electroencephalogram.

In what follows, we consider the cerebral source to be the linear expansion of a set of weighted orthogonal basic source waveforms, $\{eud_1, eud_2, \ldots, eud_p\}$. Further, we consider the basic waveforms to be given by the principal components analysis of the event-averaged waveforms obtained from a calibration process for the known set of m-th order decisions. Here, the number of basic waveforms, p, is less than or equal to the number of decisions, m, by the analysis procedure in which waveforms with minimal variance are discarded from the set since they are the result of signal noise. In a further embodiment, the expansion is based on the difference waveforms of the event averages subtracted from the grand average form. Essentially, the cerebral source is the sum of the outputs of a set of attenuators each which operates on one of the basic waveforms, such that, $$cds[K]=b_0*eud_0[K]+b_1*eud_1[K]+\ldots+b_p*eud_p[K]. \quad (2)$$

where the weight coefficients $\{b_0, b_1, \ldots, b_p\}$ are the attenuating values of the corresponding attenuators, eudo is the grand average waveform, and the set of basic waveforms $\{eud_1, \ldots, eud_p\}$ follow from the principal components analysis of the event-average differences. The development of a principal components expansion utilizes either the correlation coefficient or the cross covariance as the similarity measure. Any strong components within the event averaged waveforms will have more effect upon the value of the correlations than weak components which may be of greater significance for tracking decision making. The use of difference waveforms emphasize these important components of the data in the principal components analysis. As a result, Equation 1 now takes the form:

$$cpr[\kappa]=b_0*eud_0[\kappa]+b_1*eud_1[\kappa]+\ldots b_p*eud_p[\kappa]+a_1*cpr[\kappa-1]+a_2*cpr[\kappa-2]+\ldots a_n*cpr[\kappa-n]+e[\kappa], \quad (3)$$

where the coefficient $b_0$ weights the grand average.

The orthogonality of the basic waveforms is used to reduce the sampling Equation 3 to a set of linear equations which relate the attenuator values to the autoregressive coefficients. Multiplying Equation 3 by the i-th basic component, and summing over all samples results in the equation:

$$\sum(eud_i[\kappa]*cpr[\kappa]) = b_0 * \sum(eud_i[\kappa]*eud_0[\kappa])+ \quad (4)$$
$$b_1 * \sum(eud_i[\kappa]*eud_1[\kappa])+$$
$$\ldots +$$
$$b_i * \sum(eud_i[\kappa]*eud_i[\kappa])+$$
$$\ldots +$$
$$b_p * \sum(eud_i[\kappa]*eud_p[\kappa])+$$
$$a_1 * \sum(eud_i[\kappa]*cpr[\kappa-1])+$$
$$\ldots +$$
$$a_n * \sum(eud_i[\kappa]*cpr[\kappa-n])+$$
$$\sum(eud_i[\kappa]*e[\kappa]),$$

for all basic waveforms with an index i from 1 to p.

Since the basic waveforms are orthogonal and the noise field is uncorrelated, this expression reduces to the following form which relates the attenuation value for the ith basic waveform to the grand average attenuation and the set of autoregressive coefficients:

$$b_i=(c_{i0}-b_0*u_{i0}-a_1*c_{i1}-a_2*c_{i2}-\ldots-a_n*c_{in})/u_{ii}$$

Here, $$c_{ij}=\Sigma(eud_i[\kappa]*cpr[\kappa-j]), \text{ and}$$

$$u_{ij}=\Sigma(eud_i[\kappa]*eud_j[\kappa]), \quad (5)$$

where $u_{ij}$, is equal to zero or the power of the i th basic waveform, for all i and j greater than zero. We may repeat this process for the attenuation values of all basic waveforms, resulting in the set of linear equations, $$b_1=(c_{10}-b_0*u_{10}-a_1*c_{11}-a_2*c_{12}-\ldots-a_n*c_{1n})/u_{11}$$
$$b_2=(c_{20}-b_0*u_{20}-a_1*c_{21}-a_2*c_{22}-\ldots-a_n*c_{2n})/u_{22}$$
$$b_p=(c_{p0}-b_0*u_{p0}-a_1*c_{p1}-a_2*c_{p2}-\ldots-a_n*c_{pn})/u_{pp} \quad (6)$$

where for a orthonormal basis, $u_{ii}=1$, for all i=1,..., p; since the power of a basic waveform is unity.

Substituting the expressions of equation set 6 into Equation 3 results in an expression relating the cerebral surface potentials and the basic waveforms to the autoregressive coefficients and the grand average attenuation:

$$cpr[\kappa] = c_{10}*eud_1[\kappa]+\ldots+c_{p0}*eud_p[\kappa]+ \quad (7)$$
$$b_0*(eud_0[\kappa]-u_{10}*eud_1[\kappa]-\ldots-u_{p0}*eud_p[\kappa])+$$
$$a_1*(cpr[\kappa-1]-c_{11}*eud_1[\kappa]-\ldots-c_{p1}*eud_p[\kappa])+$$
$$a_2*(cpr[\kappa-2]-c_{12}*eud_1[\kappa]-\ldots-c_{p2}*eud_p[\kappa])+$$
$$\ldots +$$
$$a_n*(cpr[\kappa-n]-c_{1n}*eud_1[\kappa]-\ldots-c_{pn}*eud_p[\kappa])+$$
$$e[\kappa],$$

This expression may be solved by the least means square procedure for the set of autoregressive coefficients augmented by the grand average attenuation $\{a_1, a_2, \ldots, a_n, b_o\}$. The set of basic waveform attenuations $\{b_1, b_2, \ldots, b_p\}$ are then computed from Equations 5.

Further refinement in the computation of the attenuation values is made with the Jacobian iterative method for the solution of linear systems. The equation set 6 may be arranged in the matrix form:

$$A*x=d,$$

where the matrix A is given by:

$$A = \begin{vmatrix} u_{11}, & 0, & \ldots & \ldots, & 0 \\ 0, & u_{22}, & 0, & \ldots, & 0 \\ & & \ldots & & \\ 0, & 0, & \ldots & 0, & u_{pp} \end{vmatrix}$$

and the vectors by, $x = [b_1, b_2, \ldots, b_p]'$, and $d = [c_{10} - b_0 * u_{10} - a_1 * c_{11} - a_2 * c_{12} - \ldots - a_n * c_{1n},$ $c_{20} - b_0 * u_{20} - a_1 * c_{21} - a_2 * c_{22} - \ldots - a_n * c_{2n},$ $\ldots$ $c_{p0} - b_0 * u_{p0} - a_1 * c_{p1} - a_2 * c_{p2} - \ldots - a_n * c_{pn}]',$ (8)

where (') represents the vector transpose. This matrix equation 8 is converted to an equivalent system of the form $$x(\zeta) = T * x(\zeta - 1) + c,$$ (9)

which for each $\zeta = 1, 2, 3, \ldots$, constitutes an iteration process where the initial solution vector is denoted by $x(0)$. The matrix T and the vector c are derived by rearranging the linear set of Equations 6. The initial solution vector is determined by the least mean square solution of Equation 7 using the basic waveforms and the recorded cerebral surface potentials as known data sets.

The set of basic waveforms for the cerebral source is computed from event averaged potentials (EAP) which are the result of a calibration process. The event averaged potentials are computed by averaging a large number of measurements of the transient, single event, cerebral potential, each time locked to the repetitive stimulus. In actuality, the underlying single event response potential will be a variation of the average response throughout the data collection process. However, the background electroencephalogram being the product of a stochastic process, should average to zero over many repetitive trials.

For the averaging process, Equation 1 reduces to:

$$eap[K] = cds[K] + a_1 * eap[K - 1] +$$ (10)

$$a_2 eap[K - 2] + \ldots + a_n * eap[K - n],$$

where the equation applies to the entire sample for $K = 0, 1, \ldots, N-1$; and the evoked averaged response is zero for samples before the stimulus ($K < 0$). Equation 10 is inverted to derive the cerebral source (CDS) in terms of the corresponding event averaged potential (EAP). The resulting inverse filtering equation is:

$$cds[K] = (eap[K] - a_1 * eap[K - 1] -$$ (11)

$$a_2 eap[K - 2] - \ldots - a_n * eap[K - n]).$$

The autoregressive coefficients $\{a_1, a_2, \ldots, a_n\}$ are determined by analysis of a recording prior to the evoking stimulus; the background electroencephalogram tends to remain stochastically stable over a 10 to 20 second period.

A principal components analysis (PCE) is applied to the cerebral sources of the set of event averaged potentials to produce a set of orthogonal basic waveforms. In a further embodiment, the cerebral sources are time-wise averaged together to produce a grand average, and the principal components analysis is applied to the cross correlation matrix of the deviation waveforms formed from the source differences from the average. This is done to stress meaningful differences in the analysis. In a still further embodiment, the analysis is followed by a varimax rotation for factor analysis. The resulting transformations preserve the orthonormality of the basic waveforms but this is not necessarily true for the weighting coefficients.

A principal components analysis with a varimax rotation of the basic waveforms yields a temporally well separated set. The overlap is small and only a few waveforms contribute to the resultant source at any time. For this reason, the resulting set of basic waveforms may be readily interpreted in terms of the underlying cerebral sources of the stages of cognitive processing. This follows since the amplitudes and latencies of the various components of the evoked response are associated with the different stages of cognitive processing as described below:

(a) Attention: The slow negative potential preceding subject response to a stimulus has been related to attention and motivation. The slow negative potential which precedes cued evoked responses is known as the contingent negative variation (CNV), while the potential preceding voluntary initiated motor movements is known as the readiness potential (RP). The RP is the sum of a central cortex-component and a frontal component which is related to subject uncertainty. In general, the magnitude of the response is enhanced during attention to a task but reduced during inattention, whether by distraction or habituation.

(b) Stimulus response: The P100 component, the positive peak which occurs about 100 ms following the evoking stimulus, is associated with the receipt of the stimulus, and the P200 component (the positive peak at about 200 ms) is associated with the analysis of the physical characteristics of the stimulus.

The evoked response to nonrelevant stimuli has been related to vigilance. The amplitude and latency of the early negative components (N100 a and N100b) and P200b, but not the earliest positive peak (P100), relate to vigilance. A decrease in alertness correlates positively with a reduction in response amplitude and negatively with an increase in latency. The changes are most noticeable for EEG measurements which are taken from the occipital site for visual input.

The amplitude and latency of the N200 component, the negative peak between 200 ms and 250 ms, is related to the reaction time. Faster responses (i.e., shorter reaction times) are related to increased amplitude and shorter latency. The latency of all major peaks is related to reaction times.

The evoked response has been associated with workload. The difficulty of a performance task is related to the amplitude of the P200 component and the overall maximum power in the evoked response. Increased processing load generates larger late positive components during recognition and discrimination responses. In addition, the right hemisphere, but not the left, shows a large P200 component during simple recognition; and this asymmetry is enhanced during more complex processing.

The long latency, low frequency, positive peak component occurring at about 225 ms to 250 ms is related to subject confidence in visual detection tasks. The positive peak at 250 ms appears in the visual response when a subject is certain about a threshold detection judgment even when incorrect. The component also reflects additional aspects of the stimulus when processing more difficult tasks.

(c) Information Processing: It has been shown that during information processing certain characteristics of the evoked response depend upon the decision that is made. In particular, the P300 component (positive peak between 250 ms and 400 ms post-stimulus) of the evoked potential following the test stimuli has been shown to vary with cognitive activity. The P300 peak is a function of the information processing required by the workload, except in the case of time and accuracy requirements, where other factors appear to dominate the component.

For example, the amplitude of the P300 component has been shown to be greater for acceptance decisions than rejection decisions in a simple matching test. The amplitude is largest when evoked by a relevant stimulus which requires attention and decision by the subject and is also related to the difficulty of the decision. The amplitude decreases for non-relevant stimuli. In contrast, the latency increases when memory load is increased.

Finally, the P300 component is influenced by the sequence of stimuli which precedes the evoking stimulus. The presentation of a low-expectancy stimulus causes a high amplitude component, while the opposite is true for presentation of a high-expectancy stimulus. Furthermore, there is evidence that when errors occur the P300 component follows the response instead of preceding it; that is, the latency of the P300 component exceeds the reaction time on error trials. Apparently, the subject continues to process the information in the stimulus after the overt response has occurred.

Figure 6:
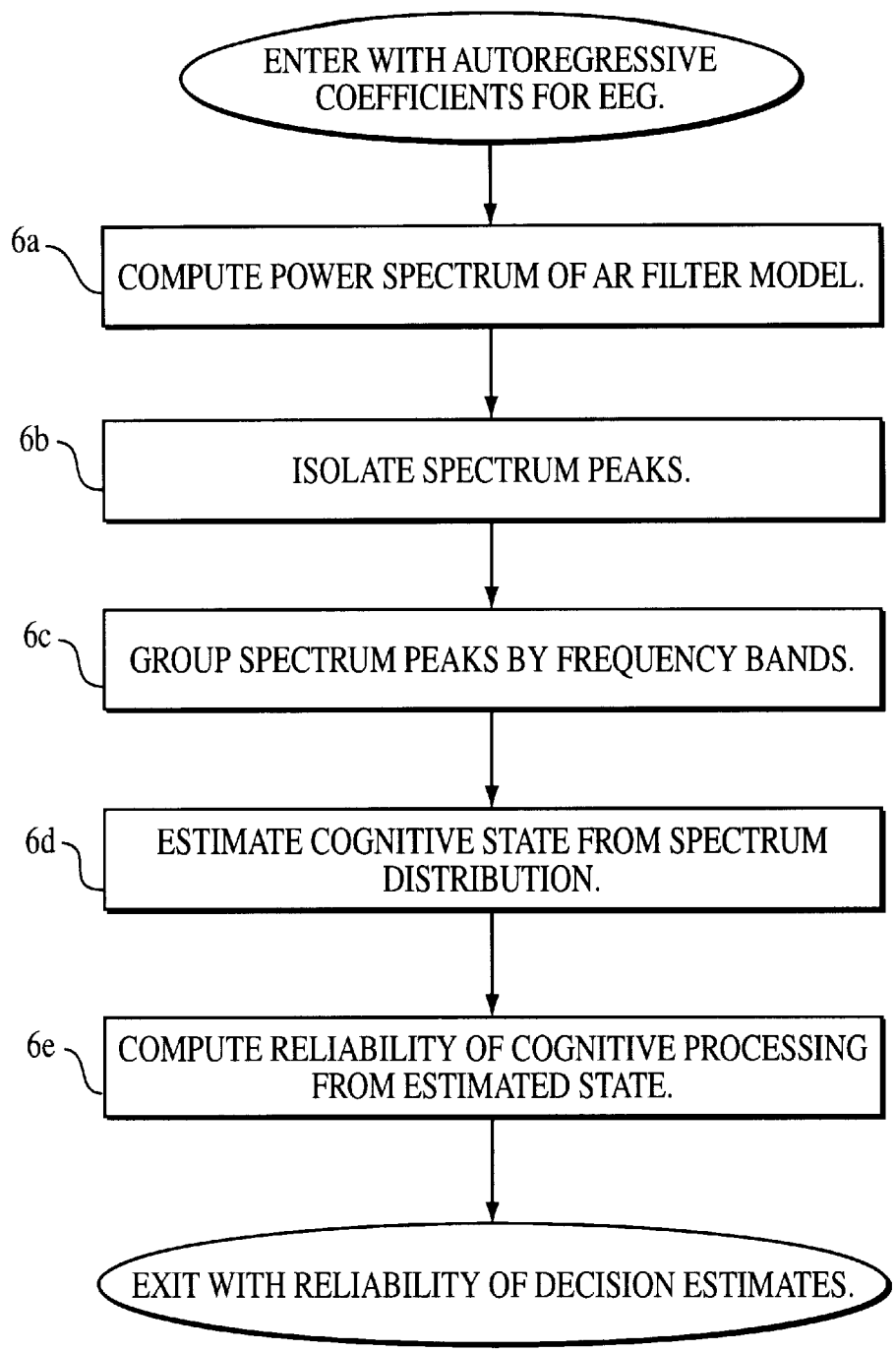
FIG. 6 is a flowchart of the expert system routine used to judge the reliability of the decision estimates.

FIG. 6 flowcharts the functions of the expert system used in software routine 15 to judge the reliability of the decision estimation. The expert system consists of two cascaded stages: a front-end, short-time spectrum analyzer for data input, followed by an inference engine with a set of production rules. The spectrum analyzer computes (6a) the power spectrum of the frequency response from the autoregressive coefficients of the autoregressive filter used to model the EEG for each cerebral recording site. The analyzer then determines (6b) the spectral peaks with a peak-picking algorithm and groups them by the frequency bands of the power spectrum that are sensitive (6c) to the states of mental alertness for cognitive processing. The distribution of these spectrum peaks differs with recording site depending upon the cognitive state. The inference engine next parses the production rules with the resulting power frequency distributions as data input (6d) for an estimate of the cognitive state, and this in turn into a measure (6e) of the reliability for cognitive processing. The selection of cognitive sensitive frequency bands for state classification and the reliability rules for cognitive processing are derived from an expert knowledge of cognitive processes.

In a further embodiment, the state estimation by the expert system uses additional information to supplement the spectrum analysis. This information is based on the application of the non-parametric method known as the Kullback Leibler-Nearest Neighbor (KL-NN) Rule to the predictive residuals from the fit of the EEG to the autoregressive processes for samples representative of the different state classes. The residuals are computed from the quadratic products of the coefficient vectors and the correlation matrix for the EEG sample.

The expert knowledge for classification of the cognitive processing state from the power spectrum analysis is based on the following. In general, the electroencephalogram as recorded from the surface of the scalp, consists of slow rhythmical waveforms that varies between 10 and 100 microvolts in amplitude and from 0.5 up to 100 Hertz in frequency. In conventional analysis, the normal frequency range of the electroencephalogram (0.5 Hz to 30 Hz) is subdivided into five rather broad frequency bands: delta (0.5–4 Hz), theta (4–8 Hz), alpha (8–13 Hz), beta (13–22 Hz), and the gamma (22–30 Hz) band. The human mental state has been shown to vary with the distribution of signal power among these frequency bands.

For example, in most normal adult subjects, the EEG is made up of rhythmic oscillating waves with a basic frequency of about 10 hertz from the alpha band (8 to 13 hertz). Typically this alpha wave oscillation has an amplitude of 50 microvolts peak-to-peak, although in about 10 percent of the population it is absent or very small. The alpha waves are best recorded from the scalp at the back of the head over the occipital lobe and over the tertiary frontal area, and are strongest when the subject is relaxed, awake and resting quietly with the eyes closed. The waves are reduced or blocked when the eyes are opened and attention is concentrated.

In particular, the alpha rhythm responses to mental activity for when a subject performs a task such as arithmetic the rhythm is attenuated leading to alpha suppression. In this process, the alpha waves are replaced by irregular gamma waves of lower voltage and higher frequency which are often associated with information processing. This alpha blockage by gamma waves is even more pronounced when the subject is excited or startled. On the other hand, as the subject becomes drowsy, the alpha rhythm is reduced and replaced with the slower, higher amplitude delta rhythm.

The more rapid rhythmic and smaller beta waves characterize the normal EEG which is recorded from the scalp regions over the central (precentral and postcentral sensorimotor areas) and frontal brain (secondary frontal area). These beta waves are associated with the sensory and motor functions of the brain, and they are blocked (i.e., desynchronized) by voluntary movements in a manner similar to the blocking of the alpha rhythm by eye openings. In addition, hippocampal theta rhythm is associated with arousal and activity.

The expert system processor uses this expert knowledge of the assignment of the spectrum peaks from different recording sites to the frequency bands for different mental states to perform membership classification on the computed spectrum distribution. That is, a pattern in the EEG of irregular, rapid waves with low amplitude correspond to alert, excited, and emotional states; regular, slower, and higher amplitude waves appear for relaxed states; and even larger and slower fluctuations appear when the subject is drowsy. Thus, the level of arousal from low to high can be inferred from the pattern of EEG activity. In a further embodiment, the member classes are: "drowsiness", "relaxed", "attentive", and "excited". The "drowsiness" state has a predominance of spectrum power in the delta band and the "relaxed" state in the alpha. The "attentive" state shows alpha suppression with strong components in the beta and gamma bands. Finally, the "excited" state has a predominance of power in the gamma band. The measured power spectrum will be distributed across these frequency bands. In turn, the logic rules judge the most likely cognitive state to be that of attentiveness, and least likely those of the end extremes, drowsiness or excitement. This is based on experiments that have shown that performance is greater at the intermediate levels of arousal than at the low and high arousal states. The processor parses the rules selecting the maximum for a judgment of the reliability of the mental state for cognitive functioning.

Figure 7:
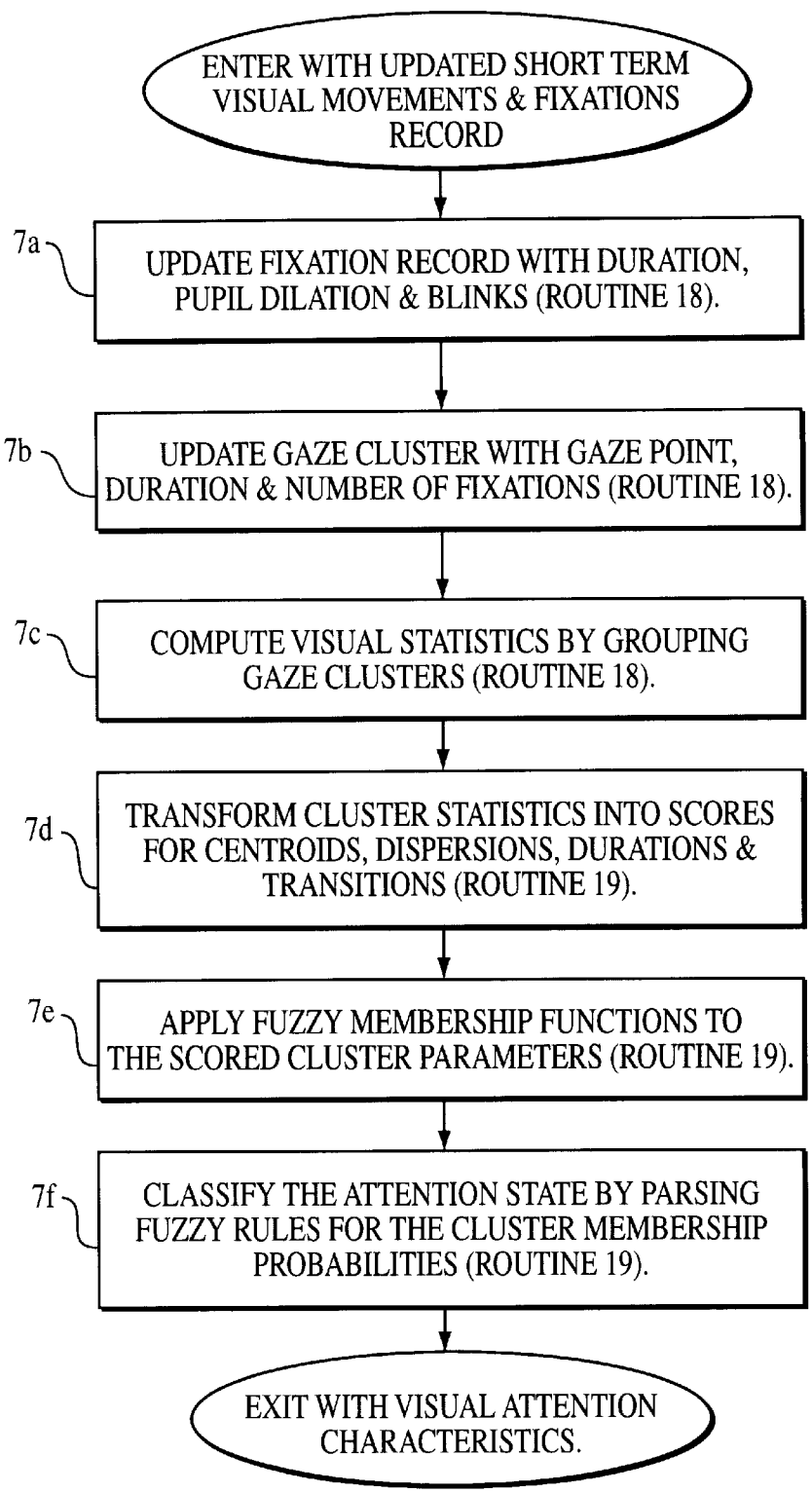
FIG. 7 is a flowchart of the fuzzy logic routine used to compute the visual attention response of the human to the display stimuli set.

FIG. 7 flowcharts the functions of computer routines 18 and 19 that are used to track the visual responses and the attention state. The routine 18 maintains a record (7a) of the operator's eye-movements ordered by time, where the record contains the locations, start times, and durations of the visual fixation points on the display, as well as the pupil size and eye blinks. The routine computes the characteristics of the present fixation, such as the fixation duration, the changes in pupil size, and the number of eye blinks at the end of the fixation. The routine clusters adjacent eye fixations into gaze points (7b) and in the process computes the gaze statistics (7c) from the short-term time record of eye-movements over the last commonly 10 seconds. These statistics include the time of occurrence of the first fixation in the cluster, the number of fixations within the gaze, the centroid of the locations of the fixations, dispersion of the locations, and time duration of the gaze clusters, and the times of transitions between gazes. In particular, the routine updates the statistics for the present gaze and the offset of the gaze centroid from the displayed stimulus. In a further embodiment, the routine groups the gaze clusters by the times that display stimuli were presented and forms grand clusters from the gaze clusters for the same stimulus by computing grand centroids and dispersions from the centroids and dispersion statistics for the clusters, and accumulates the transition counts, and the time durations. The routine blocks the gaze clusters by the times of the display stimuli.

The routine 19 transforms the cluster statistics into quantitative scores (7d) by normalizing the values for fixation counts, the dispersions, the cluster durations, and the rate of transitions, from calibration data unique to the human user. The routine applies fuzzy membership functions to the scored cluster parameters (7e) to determine fuzzy logic vector sets comprised of membership class probabilities for the fuzzy terms for each of the cluster categories of fixation count, dispersion, duration, and transition rate. The routine then parses fuzzy classification rules (7f) for the cluster membership probabilities to classify the attention state, where:

(1) the "erratic" state, in which the human is performing undisciplined search, describes clusters with low fixation counts, short time durations, and high transition rates;

(2) the "search" state, in which the human is performing disciplined search, describes clusters with medium transition rates, medium fixation counts, medium durations, and dispersions close to that for a normal search;

(3) the "focused" state, in which the human is focused on a task, describes clusters with low transition rates, medium or high fixation counts, medium durations, and dispersions that are near that for the normal gaze;

(4) the "aiding task" state, in which the human is focused on the aiding task, describes clusters suitable for a focused state which furthermore form grand clusters with centroids, dispersions, durations and transitions that closely track the displayed stimuli; and (5) the "confounded" state, in which the human is staring straight ahead and not attending to the tasks either due to confusion or fatigue, describes clusters with few transitions, very long time durations, low or medium fixation counts, and dispersions that are much narrower than that for normal gaze.

Figure 8:
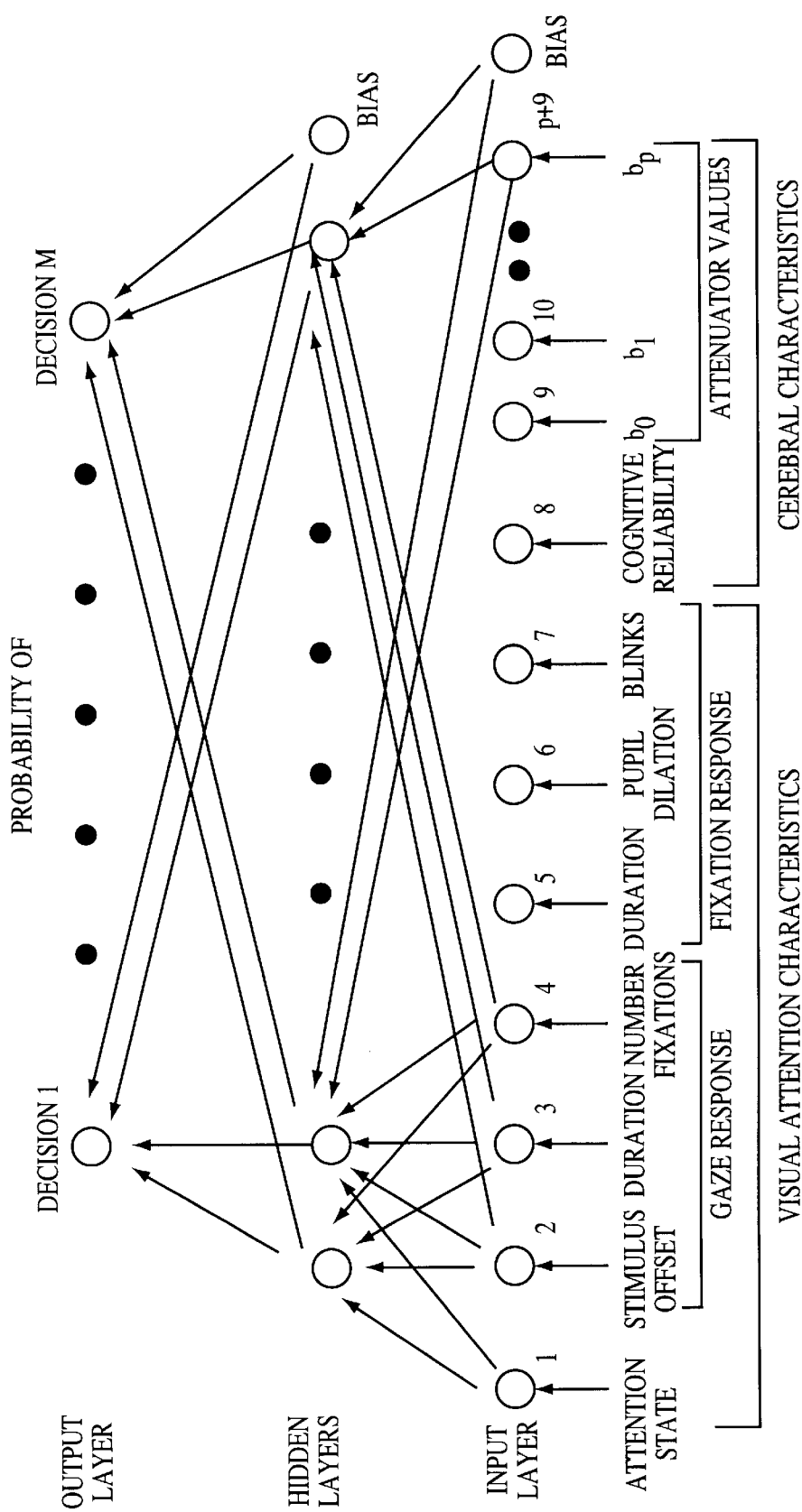
FIG. 8 is a schematic of the artificial neural network used as a decision classifier.

FIG. 8 is a schematic of the artificial neural network (ANN) which is used in the routine 20 as a discriminant function for representing the statistics of the decision making process. In the embodiment of FIG. 8, the present invention uses the Rumelhart's feed-forward, back-error propagation system. This system is a layered architecture that contains a layer of input nodes, several hidden layers of intermediate nodes, and a layer of output nodes. In addition, a bias node, providing a constant reference value, is part of each hidden layer and the input layer. Each node of one layer is fully connected to the nodes of the succeeding layer. The inputs flow forward from layer to layer to the outputs during recall. Although some work has been done indicating that a maximum of three hidden layers can be used to solve arbitrarily complex classification problems, most back propagation networks have one or two hidden layers, with the number of hidden layer nodes somewhere between the total number of input and output processing nodes. The number of nodes required in the hidden layers increases with the complexity of the relationship between the inputs and the outputs.

In one embodiment, the transfer function of the processing nodes is the non-linear sigmoid function with low and high saturation limits of zero and one. The output of a node in the inner or outer layers is a function of the weighted inputs. The inputs to the node are the outputs from the nodes in the lower layer which are weighted by the strengths of the interconnections. The weighted sum for the input is applied to an activation function which given by the weighted sum of the node inputs, produces an activation level for the node. In turn, the activation is passed through the transfer function to produce the node output.

FIG. 8 shows the inputs of the network to be the present response and state characteristics of both the cerebral potential and the visual attention. The cerebral inputs are: (1) the source attenuator values ($b_0, b_1, \ldots, b_p$) for the present basic waveform representation of the cerebral sources (inputs 9 thru p+9) for each recording site, and (2) the estimated reliability for decision making of the cognitive state (input 8). While the figure shows attenuator values for only one recording site, there are a set of such values for each cerebral recording site in a multiple array configuration of electrodes. The visual attention inputs are the measures of the present visual fixation, the present gaze, and the attention state. The measures of the fixation are: (1) the duration (input 5), (2) changes in the pupil size (input 6), and (3) number of eye-blinks (input 7), all associated with instantaneous information processing. In turn, the gaze measures are: (1) the gaze duration (input 3), (2) the number of fixations (input 4) within the gaze cluster, and (3) the gaze center offset (input 2) from the displayed stimulus, all associated with attention direction. Finally, the attention state is included as input 1 since it is an important measure of the responsiveness of the human to the stimulus. The input for the gaze center offset is a numeral indicating either the central, far, or peripheral vision fields. Here, the stimulus is either within the central vision associated with the span of visual attention, or it lies beyond in the far or peripheral fields. A separate numeral value indicates the absence of a displayed stimulus. Further, the input for the attention state is a numeral used to designate the state classes. This approach of using categories that correspond to the underlying physiological mechanisms increases the accuracy of the network classifications. Finally, the outputs of the network (decision 1, . . . , m) are the probabilities of the occurrences of the set of possible cognitive decisions, including missed responses and errors as decision categories, which can be made in response to the displayed stimulus.

The routine 21 selects the most likely decision from the outputs of the classifier; in one embodiment the strongest output of the classifier exceeding a threshold is selected as the best estimate of the decision made, otherwise the choice of no decisive decision is made. The routine 22 then determines the aiding to be provided to the human operator from an expert system with production rules based on the disparities among the decision estimations and the decisions that are expected from task scripts for the displayed stimulus. In one embodiment, the estimated decision is compared to that which would be expected from a script listing a sequence of stimuli and correct responses for the task performance. The script may include display choices for user feedback that vary with the degree of disparities between the expected and the estimated decision. In a further embodiment, the routine 21 is collapsed into routine 22 and the aiding is determined from a comparison of the classifier's probabilities for the full set of possible decisions. The complexity level of the script design is determined by the type of application supported by the present invention. Referring back to FIG. 2, the figure shows that the decision aiding output 6 from the computer 5 is used as an input to the host computer 8 which is controlling the stimulus driver 3 of the displayed stimuli.

The present invention is used for the unintrusive measurement of cognitive functions during training or testing regimens. In this process, the host computer records the decisions that are estimated by the present invention for the human subject and those dictated by the task script that he is following. The recorded data is analyzed statistically to determine the subject's performance.

The present invention is used to unintrusively monitor the state of a trained human operator for fatigue when he is performing display interaction tasks. In this process, the host computer performs a time trend analysis of the differences between the estimated decisions and those expected in response to the display stimuli from the task script. An increase in the differences over time may indicate fatigue. In this way, the present invention functions as part of an electronic "safety net" to detect degradation in operator performance.

The present invention is used for the automatic aiding of cognitive functions by human operators in computerized display interaction during high workload to maintain-both task performance and situational awareness. A discrepancy between the estimated and expected response during the performance of the scripted task causes a cognitive aid to be displayed. Similarly, a discrepancy in recognizing a situational cue generates appropriate aiding. In this manner, the present invention is used to confirm that the mental decision made is a member of the set that is appropriate for processing the displayed stimulus according to the task script. Here, the present invention is used as a component of an electronic "intelligent" human-computer interface for cognitive functions.

The application of the present invention to automatic aiding is based in part upon the use of the amplitude of the P300 wave (positive wave 250 to 400 msecs following stimulus onset) of the evoked potential as a discriminating metric. The P300 will differ in amplitude depending upon whether a displayed stimulus is recognized as being a member of a task related category or not. For this purpose, the display task is structured in a manner so as to elicit changes in the P300 wave by the need for category selection.

As an example, the present invention may be used for automatic aiding during vigilance by a crew supervising an automatically controlled process, to ensure that they respond properly to an emergency. Some examples of automated processes are automated flights on a long distance commercial aircraft, an automated power plant, and a control center for a nuclear reactor. The digital computer controlling the process displays status indicators to aid the crew in their tasks and generates critical event alerts for intervention when the computerized process moves out of the controllable limits. However, alerts are rare and the crew quickly becomes bored and easily distracted. For this reason, the role of supervising an automatically controlled process soon reduces over time to that of vigilantly monitoring the displays. Because the crewmembers fail to actively monitor the automated system, they are less able to transit from the scanning behavior of supervising to that needed during an emergency of detecting, diagnoses, and correcting the system failure.

The visual and cerebral responses of a crewmember to an alert are used by the present invention as measures of his cognitive processing. The visual response and the attenuations of the cerebral sources for the early components of the evoked potential are measures of his attention and stimulus response. For example, it is likely that a crewmember has noticed a flashing alert light if he turns toward it. Further, the early components would be time locked to the flashing light. The cognitive processing of the critical event is measured by the attenuations for the sources of the P300 wave; the cognitive state estimate is a measure of the reliability of the computations. The amplitude of the P300 wave will differ depending upon whether the alert is recognized as such or not. On this basis, the mental act of responding to the alert is processed by the present invention. In turn, the process computer displays action aids as specified by the present invention from the estimated mental activity and that needed for the task script for responses to the alerts. For example, the alert is passed to the crew supervisor if the operating crewmember is not attentive. However, a check list of needed actions is displayed when the crew-member responds. This automatic aiding by the present invention supports the crew by facilitating and speeding the performance of their tasks in response to the alert.

Another application of the present invention using the P300 metric can provide aiding to the fire support officer for air defense in an automated tactical operations center. One of the tasks that the officer must perform in the automated system is to confirm a list of targets that has been selected by the computer for fire engagement. The targets are shown as symbology on a spatial map display tagged in order of their threat priority following threat evaluation and target assignment. The threat evaluation is computed from factors that are determined by radar returns, such as location, speed, direction of travel, IFF designation, and engine type. The fire support officer must review the assignment to ensure that the targets meet the threat criteria. In this process, he considers other factors known to him but not necessarily in the computer data base. This review is a time critical task since the disposition of aviation threats changes rapidly. As the officer reviews the list by gazing at each of the target symbology in turn, the amplitude of the P300 wave of his evoked potential will depend upon whether a tagged target is recognized as being within the threat criteria or not. In turn, the mental act of rejecting the threat designation for a target is processed by the present invention. The resulting automated aiding will cause the computer to display a table listing the computed criteria weights for review by the officer. Again, this automated aiding supports the officer by facilitating and speeding the performance of his task.

An automatic calibration method is used to determine human operator specific constants that are used in the computations. These include: (1) the constants used in the filter functions of digital signal processor 2 for cerebral artifact isolation, (2) the visual normalization constants used with routine 19 for visual state classification, (3) the event average response potentials used in the solution method of software routine 1–6 for parameterizing the cerebral signal, and (4) the data base used to train the interconnective weights for the artificial neural network of routine 20. In this calibration, the human operator first performs a sequence of muscular activities for brief periods while cerebral and artifact signals are measured to establish record files for artifact analysis. This sequence is as follows: (1) no activities for electrocardiogram (EKG) recordings, (2) facial and head movements for the corresponding electromyograms (EMG), (3) manual tracking movements for shoulder and arm EMG, and (4) finally visually tracking for the electrooculogram (EOG). A set of regression analyses are then performed on the signal measurements to determine the parameters of the estimation and smoothing filters needed to isolate the electroencephalogram from the cerebral artifacts.

The human operator next performs a set of visual functions in response to a set of displayed stimuli in which he first searches for a target stimulus among irrelevant clutter, and then performs a set of visual gazing tasks. The result is a set of visual normalization constants for the fixation counts, the dispersions, the cluster durations, and the rate of transitions for different viewing conditions, as well as the search and gaze dispersion sizes.

The human operator then responds to a repetitive set of displayed stimuli for which he has been instructed to make specific decisions while his visual responses, skin surface potential measurements, and decision responses, made apparent by motor actions, are recorded. The potential measurements are used to construct event average evoked potentials for the decision responses including missed responses and errors as separate categories. The electroencephalogram is first corrected for artifacts using estimating and smoothing filtering and time-locked to the displayed stimulus. The electroencephalograms for the same decision responses are then event averaged to estimate the average evoked potentials for the different decision cases.

Figure 9:
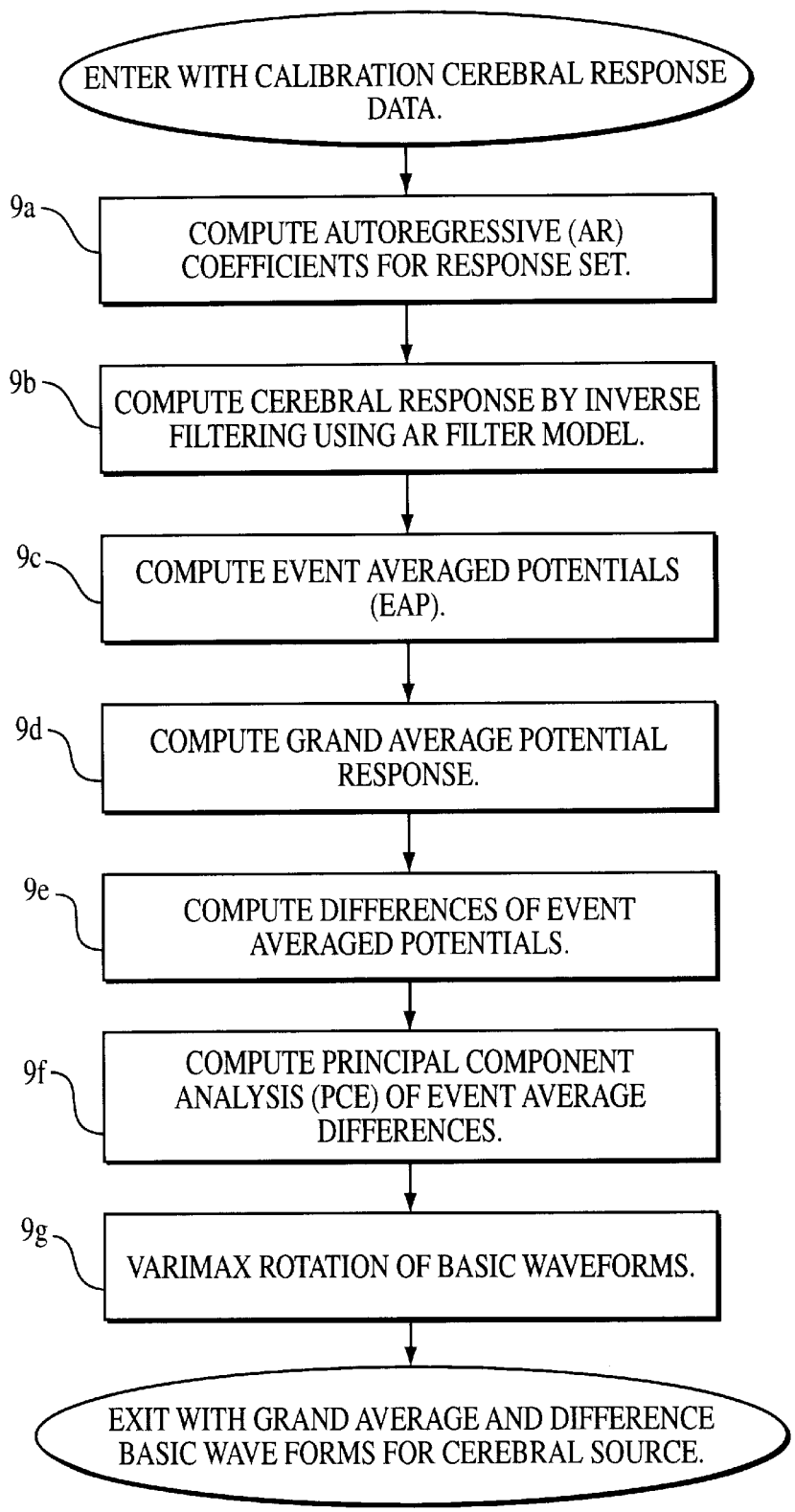
FIG. 9 is a flowchart of the routine used to compute the basic waveforms from the principal components analysis of the event averaged cerebral source differences.

The set of orthogonal basic waveforms for the cerebral sources of the decision responses are determined from the average evoked potentials and the corresponding autoregressive coefficients using the method flowcharted in FIG. 9. The autoregressive coefficients are computed (9a) from the EEG data header to the stimuli events, and again from the data tail for checking to ensure stochastic stability. The cerebral sources are computed (9b) with Equation 11 from the autoregressive coefficients and the corresponding event average potentials (9c). The grand average potential is computed (9d), as are the differences (9e) of the event average potentials. A principal components expansion (PCE) is applied (9f) to the set of event averaged difference potentials to produce a set of orthogonal basic waveforms. A vaximax rotation is then applied (9g) to the basic waveforms for time separation of the sources. The attenuator-values are then computed with the solution method of FIG. 4 for each test case from the corresponding single event cerebral potential and the set of sources.

The classifier consisting of the artificial neural network is trained from the data set pairs of input and output values for each stimulus response. The input contains the attenuator-values for the single event cerebral potential, the cognitive reliability, the fixation and gaze visual responses, and the attention state for each stimulus; the outputs are the corresponding decision responses. The network as embodied in FIG. 8 is trained by a supervised back-propagation method which propagates the output error for a training set of paired inputs and outputs back through the network. The method adjusts the connection weights for the nodes of the network so as to minimize the error between the actual output and the data output for each training input set. This is accomplished by first forward propagating the input through the hidden layers to the output layer, then determining the error at the output layer, and finally propagating the errors back through the network from the output layer to the input layer. The changes in the connection weights are computed for the output and hidden layer nodes from the node errors. In this way, the back propagation algorithm modifies the connection weights to reduce the output error for each input and output pair in the training set.

It will be readily seen by one of ordinary skill in the art that the present invention fulfills all of the objects set forth above. After reading the foregoing specification, one of ordinary skill will be able to effect various changes, substitutions of equivalents and various other aspects of the present invention as broadly disclosed herein. It is therefore intended that the protection granted hereon be limited only by the definition contained in the appended claims and equivalents thereof.

Having thus shown and described what is at present considered to be the preferred embodiment of the present invention, it should be noted that the same has been made by way of illustration and not limitation. Accordingly, all modifications, alterations and changes coming within the spirit and scope of the present invention are herein meant to be included.

What is claimed is:

1. An apparatus for the automatic aiding of human cognitive functions during the operation of computerized displays from displayed stimuli, comprising:

a digital processor with inputs of recorded human biosignals from analog amplifiers appropriately placed to record the electroencephalogram, electrooculogram, and muscular potentials, that applies filtering to remove the artifacts from the electroencephalogram, that maintains a file of the processed signal, and that outputs a windowed cerebral potential commonly of one second in duration;

a digital processor that inputs the type of stimulus being displayed for the task being performed, that maintains a file of cerebral sources for the different stimuli-types, and which outputs the basic waveforms for the corresponding cerebral sources which are evocable by the stimuli-type;

a digital processor that inputs the said windowed cerebral potential and the said set of basic waveforms, that computes parameters for an autoregressive model of the cerebral potential which is driven by the summed outputs of parallel attenuators with the basic waveform sources as inputs, and which outputs the computed parametric values of the attenuations and autoregressive coefficients;

an expert system processor that consists of a front end spectrum analyzer cascaded in series with an inference engine and production rules, that inputs the said autoregressive coefficients to the said spectrum analyzer, that computes the power spectrum of the autoregressive coefficients as data input to the said inference engine, that estimates the cognitive state and from that a reliability measure by parsing the said production rules, and outputs the measure;

a digital processor that inputs the recorded visual responses of the human from a recorder of the head and eye movements, fixations, pupil sizes, and eye blinks; which maintains a file of the visual responses, which computes visual indexes from the file, in particular, the location and duration of the visual fixations and the associated pupil sizes and the number of eye blinks, clutters the fixations into gaze points, determines the gaze durations, and the transitions between the same; and which outputs these indexes;

a fuzzy logic processor that consists of a front-end statistical analyzer, a set of fuzzy membership functions, and a set of fuzzy classification rules; that inputs the said visual indexes to the said statistical analyzer, computes gaze statistics from the indexes, and transforms the gaze statistics into normalized scores; that applies the fuzzy membership functions to the scores to form fuzzy logic vector sets comprised of membership class probabilities; that parses the fuzzy classification rules for the membership probability vectors into an estimate of the attention state; and outputs the estimated state;

a digital classifier that inputs the said attenuation values, the said cognitive reliability, the said indexes of the visual response, and the said attention state, all to an artificial neural network which with interconnection weights, estimates the probabilities of the occurrences of all possible decisions that can be made in response to the displayed stimulus, and outputs the same;

a digital processor with input of the said decision probabilities, that selects the most likely decisions, and outputs the same; and an expert system processor that consists of an inference engine and production rules with input of the said most likely decisions, that determines the decision aiding from rules based on the disparities among the most likely decision estimates and the decisions that are expected from task scripts for the displayed stimulus, and outputs the cognitive aiding to the computer controlling the display driver.

2. A method for estimating a cognitive decision made by a human operator in response to a displayed stimulus, from his single event, evoked potential response and the corresponding visual process, comprising the steps of:

mapping the elements of a set of parameters uniquely one-to-one onto the elements of a set of orthogonal basic waveforms, where the set of said basic waveforms are derived from a principal components analysis of the event average, evoked difference potential responses made by the human to the set of stimuli of which the displayed stimulus is an element, such that the set of said basic waveforms represent the cerebral sources of all possible decisions which can be made by the human in response to the displayed stimulus;

mapping the said set of parameters uniquely one-to-one onto a set of attenuators, where the input to each said attenuator is the correspondingly mapped said basic waveform source, the values of the said parameters are given by the attenuations for the corresponding sources, and the sum of the outputs of the attenuators is the deterministic input to an autoregressive filter used to model the single-event, evoked potential as a cerebral process;

estimating the values of the said attenuation parameters for the single event, evoked potential by:
(1) computing weights from the corresponding electroencephalogram and the said basic waveform sources for the stimuli set for the said parallel attenuator-autoregressive filter model,
(2) computing a least mean square solution to the autoregressive coefficients of the said model using the said weights,
(3) computing the attenuation values for the said basic waveforms from the said weights and autoregressive coefficients, and
(4) applying an iteration technique with the above said solutions as initial conditions;

computing the reliability of the estimation of the said attenuation parameters by computing the power spectrum of the electroencephalogram from the said autoregressive coefficients, and classifying the cognitive state of the human operator from the said power spectrum components and computing the reliability of the estimated decision from the said classified cognitive state with an inference engine and a set of production rules based on expert knowledge of the cognitive processes as a function of the cognitive state;

computing the visual response to the displayed stimulus consisting of the fixation and gaze indexes, by:
(1) maintaining a record of the operator's eye-movements ordered by time, where the record contains the locations, start times, and durations of the visual fixation points on the display, as well as the pupil size and eye blinks,
(2) computing the indexes of the present fixation, such as the fixation duration, the changes in pupil size, and the number of eye blinks, and
(3) clustering adjacent eye fixations into a gaze point and computing: the gaze indexes of the centroid displacement from the location of the displayed stimulus, the number of fixations constituting the gaze, the time duration, and the dispersion of the fixations about the centroid;

estimating the visual attention state with fuzzy-logic from the immediate gaze history commonly over the last 10 seconds, by:
(1) computing the statistics of the gaze clusters to include the time of occurrence of the first fixation in the cluster, the number of fixations within the gaze, the centroid of the locations of the fixations, dispersion of the locations, and time duration of the gaze clusters, and the times of transitions between gazes,
(2) grouping the gaze clusters by the times that display stimuli were presented and forming grand clusters from the gazes for the same stimulus by computing grand centroids and dispersions from the centroids and dispersion statistics for the clusters, and accumulates the transition counts, and the time durations,
(3) transforming the cluster statistics into quantitative scores by normalizing the values for fixation counts, the dispersions, the cluster durations, and the rate of transitions, from calibration data unique to the human user,
(4) applying fuzzy membership functions to the scored cluster parameters to determine fuzzy-logic vector sets comprised of membership class probabilities for the fuzzy terms for each of the cluster categories of fixation count, dispersion, duration, and transition rate, and
(5) parsing furzzy classification rules for the cluster membership probabilities to classify the attention state; and applying the said attenuation parameters, said estimation reliability, said fixation and gaze response indexes, and said attention state as inputs to an artificial neural network used as a classifier, the outputs of which are the probabilities of the occurrences of all possible decisions which can he made in response to the displayed stimulus.

3. A method for the automatic aiding of human cognitive functions during the operation of computerized displays, by estimating the cognitive decisions made in response to the displayed stimuli, comprising the steps of:

establishing a record of normalization constants for the index numbers of the visual process, by:
(1) having the human operator performs a set of visual functions in response to a set of displayed stimuli in which he searches for a target stimulus among irrelevant clutter and then performs a set of visual gazing tasks,
(2) recording the visual responses of the human operator as he performs these tasks, where the visual responses are the eye-movements, the fixations, and the pupil sizes and number of eye blinks associated with the fixations, and
(3) clustering the eye fixations into gaze points, and for the gazes computing the fixation counts, the dispersions, the cluster durations, and the rate of transitions for the different viewing conditions, as well as the search and gaze task dispersion sizes, and setting the normalization constants equal to the corresponding computed values;

establishing a record set of orthogonal basic waveforms for the cerebral sources of the decision responses made to the set of display stimuli, by:
(1) recording a sequence of single-event evoked, transient cerebral potentials which are event-locked to the repeated presentations in turn of all elements of the stimuli set for multiple occurrences of all possible decisions as responses by the human operator,
(2) computing an event-average response potential for each of the possible decisions and each of the stimuli set elements from the corresponding set of all said single-event evoked, transient cerebral potentials,
(3) computing a grand average response potential from the set of said event-average responses, and in turn the set of event average difference potentials,
(4) computing the set of basic waveforms from the principal components analysis of the set of said event average difference potentials,
(5) computing the autoregressive coefficients for the electroencephalograms of the headers to the said single event recordings, and
(6) computing a set of waveforms for the cerebral sources by inverse filtering of the said set of basic waveforms with the said autoregressive coefficients;

supervised training of an artificial neural network used to represent the decision making process, by:
(1) computing a vector set of attenuations for each said single-event, evoked transient cerebral potential used in the computation of the record file of cerebral sources,
(2) augmenting the said vector set with the reliability of the cognitive state for the power spectrum computed from the said autoregressive coefficients,
(3) augmenting the said vector set with the indexes of the visual responses to the said displayed stimuli for each of the said single-event evoked responses,
(4) augmenting the said vector set with the visual attention state for the responses to the said displayed stimuli for each of the said single-event evoked responses,
(5) forming matched pairs between the said vector sets and the corresponding decision responses made for each of the said single-event evoked responses, and
(6) using the data matrix so formed from the said matched pairs, as an epoch of inputs consisting of the said attenuations, reliability, visual response indexes, and attention state, matched to the corresponding said decision response as output, for the training of the interconnection weights of the network;

continually recording the human electroencephalogram, electrooculogram, and muscular potentials from analog amplifiers appropriately placed, applying filtering to remove the artifacts from the said electroencephalogram, maintaining a file of the processed signal, and computing a windowed cerebral potential signal commonly of one second in duration;

continually recording the visual responses of the human from a recorder of the head and eye movements and maintaining a time ordered file of the said visual responses: fixations, pupil sizes, and eye blinks, and determining visual indexes from the file by:
(1) computing the indexes of the present fixation, such as the fixation duration, the changes in pupil size, and the number of eye blinks, and
(2) clustering adjacent eye fixations into gaze points and computing the gaze centroid displacement from the location of the displayed stimulus, the number of fixations constituting the gaze, the time duration, and the dispersion of the fixations about the centroid;

presenting a display stimulus to the human operator from the set of known stimuli, determining the type of the stimulus being displayed for the task being performed, and determining the basic waveforms for the corresponding cerebral sources which are evocable by the stimuli-type;

mapping the elements of a set of parameters uniquely one-to-one onto the elements of the set of said orthogonal basic waveforms, mapping the said set of parameters uniquely one-to-one onto a set of attenuators, where the input to each said attenuator is the correspondingly mapped said basic waveform source, the values of the said parameters are given by the attenuations for the corresponding sources, and the sum of the outputs of the attenuators is the deterministic input to an autoregressive filter used to model the single event, evoked potential as a cerebral process;

estimating the values of the said attenuation parameters for the single event, evoked potential by:
(1) computing weights from the corresponding electroencephalogram and the said basic waveform sources for the stimuli set for the said parallel attenuator autoregressive filter model,
(2) computing a least mean square solution to the autoregressive coefficients of the said model using the said weights,
(3) computing the attenuation values for the said basic waveforms from the said weights and autoregressive coefficients, and
(4) applying an iteration technique with the above said solutions as initial conditions;

computing the reliability of the estimation of the said attenuation parameters by computing the power spectrum of the electroencephalogram from the said autoregressive coefficients, and classifying the cognitive state of the human operator from the said power spectrum components and computing the reliability of the estimated decision from the said classified cognitive state with an inference engine of an expert system and a set of production rules based on expert knowledge of the cognitive processes as a function of the cognitive state;

estimating the visual attention state with fuzzy-logic from the immediate gaze history commonly over the last 10 seconds, by:

(1) computing the statistics of the gaze clusters to include the time of occurrence of the first fixation in the cluster, the number of fixations within the gaze, the centroid of the locations of the fixations, dispersion of the locations, and time duration of the gaze clusters, and the times of transitions between gazes, (2) grouping the gaze clusters by the times that display stimuli were presented and forming grand clusters from the gazes for the same stimulus by computing grand centroids and dispersions from the centroids and dispersion statistics for the clusters, and accumulates the transition counts, and the time durations, (3) transforming the cluster statistics into quantitative scores by normalizing the values for fixation counts, the dispersions, the cluster durations, and the rate of transitions, from calibration data unique to the human user, (4) applying fuzzy membership functions to the scored cluster parameters to determine fuzzy-logic vector sets comprised of membership class probabilities for the fuzzy terms for each of the cluster categories of fixation count, dispersion, duration, and transition rate, and (5) parsing fuzzy classification rules for the cluster membership probabilities to classify the attention state;

applying the said attenuation parameters, said estimation reliability, said fixation and gaze response indexes, and said attention state as inputs to the said artificial neural network used as a classifier, the outputs of which are the probabilities of the occurrences of all possible decisions which can he made in response to the displayed stimulus; and selecting the most likely decisions, and determining the cognitive aid to he provided to the human with an inference engine of an expert system and a set of production rules based on the discrepancy between the estimations of the most likely decisions made and the decisions expected from task scripts for the said display stimulus.

* * * * *